United States Patent
Charles

(10) Patent No.: US 11,877,956 B2
(45) Date of Patent: Jan. 23, 2024

(54) VITREORETINAL INSTRUMENTS FOR ILLUMINATION, FLUID ASPIRATION, AND PHOTOCOAGULATION

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/807,172

(22) Filed: Jun. 16, 2022

(65) Prior Publication Data

US 2023/0040005 A1 Feb. 9, 2023

Related U.S. Application Data

(60) Provisional application No. 63/230,138, filed on Aug. 6, 2021.

(51) Int. Cl.
*A61B 90/30* (2016.01)
*A61F 9/008* (2006.01)

(52) U.S. Cl.
CPC .... *A61F 9/00821* (2013.01); *A61B 2090/306* (2016.02); *A61F 2009/00863* (2013.01)

(58) Field of Classification Search
CPC ...................... A61F 9/00821; A61B 2090/306
USPC ............................................................ 606/4
See application file for complete search history.

(56) References Cited

U.S. PATENT DOCUMENTS

| | | |
|---|---|---|
| 5,318,560 A | 6/1994 | Blount et al. |
| 5,732,170 A | 3/1998 | Okude et al. |
| 7,141,048 B1 * | 11/2006 | Charles ............... A61F 9/00736 606/4 |
| 7,285,107 B1 | 10/2007 | Charles |
| 7,470,269 B2 | 12/2008 | Auld |
| 7,731,710 B2 | 6/2010 | Smith |
| 8,297,854 B2 | 10/2012 | Bickham et al. |
| 8,398,240 B2 | 3/2013 | Smith |
| 8,485,972 B2 | 7/2013 | Papac et al. |
| 8,900,139 B2 | 12/2014 | Yadlowsky |
| 9,031,371 B2 | 5/2015 | Yonezawa et al. |
| 9,066,678 B2 | 6/2015 | Auld |
| 9,364,982 B2 | 6/2016 | Schaller |
| 9,730,834 B2 | 8/2017 | Charles |

(Continued)

FOREIGN PATENT DOCUMENTS

EP 2215995 A1 8/2010

OTHER PUBLICATIONS

Alcon Vitreoretinal Product Catalog, Copyright 2008, pp. 27-29.

*Primary Examiner* — Nadia A Mahmood

(57) ABSTRACT

The present disclosure relates generally to small-gauge instrumentation for surgical procedures, and more specifically, to vitreoretinal instruments for retinal repair and reattachment procedures, as well as associated methods of use. Certain embodiments of the present disclosure provide a curved or articulating probe configured to provide illumination, fluid aspiration, and endophotocoagulation. Accordingly, the probe enables aspiration of subretinal fluid that re-accumulates after initial drainage and during endophotocoagulation without the need to exchange surgical instruments or insert an additional instrument into the intraocular space. Furthermore, the combined functionalities of the probe enable a surgeon to simultaneously perform scleral depression with the surgeon's other hand while aspirating fluid and/or performing retinal endophotocoagulation.

14 Claims, 8 Drawing Sheets

(56) References Cited

U.S. PATENT DOCUMENTS

| | | |
|---|---|---|
| 9,795,505 B2 | 10/2017 | Yu et al. |
| 10,016,248 B2 | 7/2018 | Mirsepassi |
| 10,039,669 B2 | 8/2018 | Heeren |
| 10,085,883 B2 | 10/2018 | Auld |
| 10,238,543 B2 | 3/2019 | Farley |
| 10,295,718 B2 | 5/2019 | Mirsepassi |
| 10,307,290 B2 | 6/2019 | Kern |
| 10,376,414 B2 | 8/2019 | Hallen |
| 10,413,446 B2 | 9/2019 | Bouch et al. |
| 10,869,735 B2 | 12/2020 | Diao et al. |
| 10,888,219 B2 | 1/2021 | Smith et al. |
| 11,033,427 B2 | 6/2021 | Charles et al. |
| 11,160,686 B2 | 11/2021 | Cook et al. |
| 11,471,242 B1 | 10/2022 | Diao |
| 11,517,392 B2 | 12/2022 | Mirsepassi et al. |
| 2006/0184162 A1 | 8/2006 | Smith |
| 2008/0177257 A1 | 7/2008 | Smith et al. |
| 2009/0093800 A1* | 4/2009 | Auld ..................... A61F 9/008 606/15 |
| 2011/0125139 A1 | 5/2011 | Auld |
| 2017/0172792 A1* | 6/2017 | Mirsepassi ........... A61B 3/0008 |
| 2018/0042768 A1 | 2/2018 | Charles |
| 2018/0078410 A1 | 3/2018 | Gavanescu |
| 2018/0296391 A1 | 10/2018 | Charles |
| 2018/0338859 A1 | 11/2018 | Mirsepassi |
| 2019/0046352 A1 | 2/2019 | Mordaunt et al. |
| 2019/0201238 A1 | 7/2019 | Bacher et al. |
| 2019/0282322 A1 | 9/2019 | Mirsepassi |
| 2019/0343681 A1* | 11/2019 | Heriot ................. A61F 9/00727 |
| 2021/0290438 A1 | 9/2021 | Hallen |

* cited by examiner

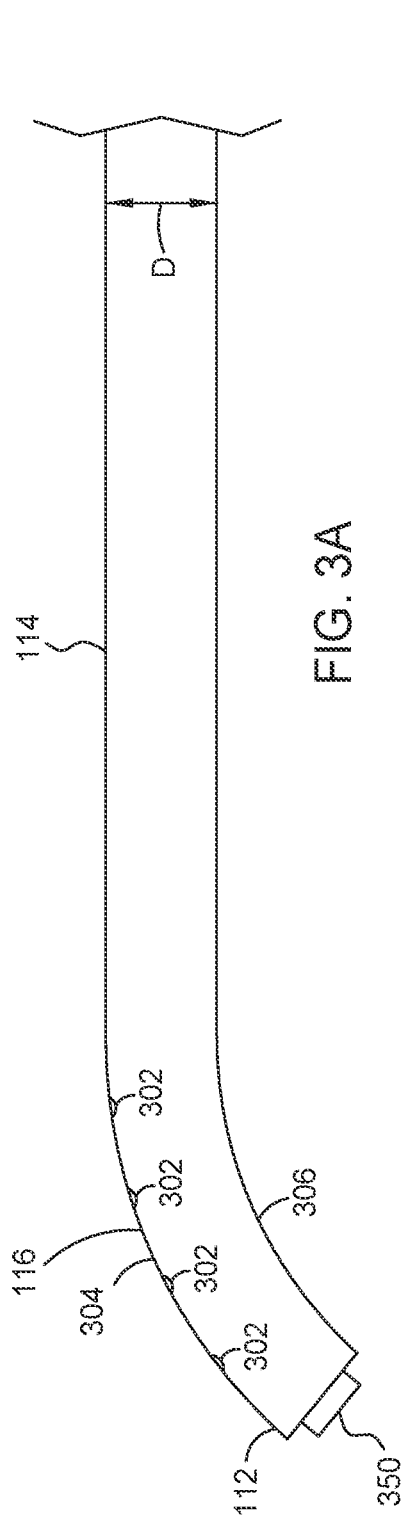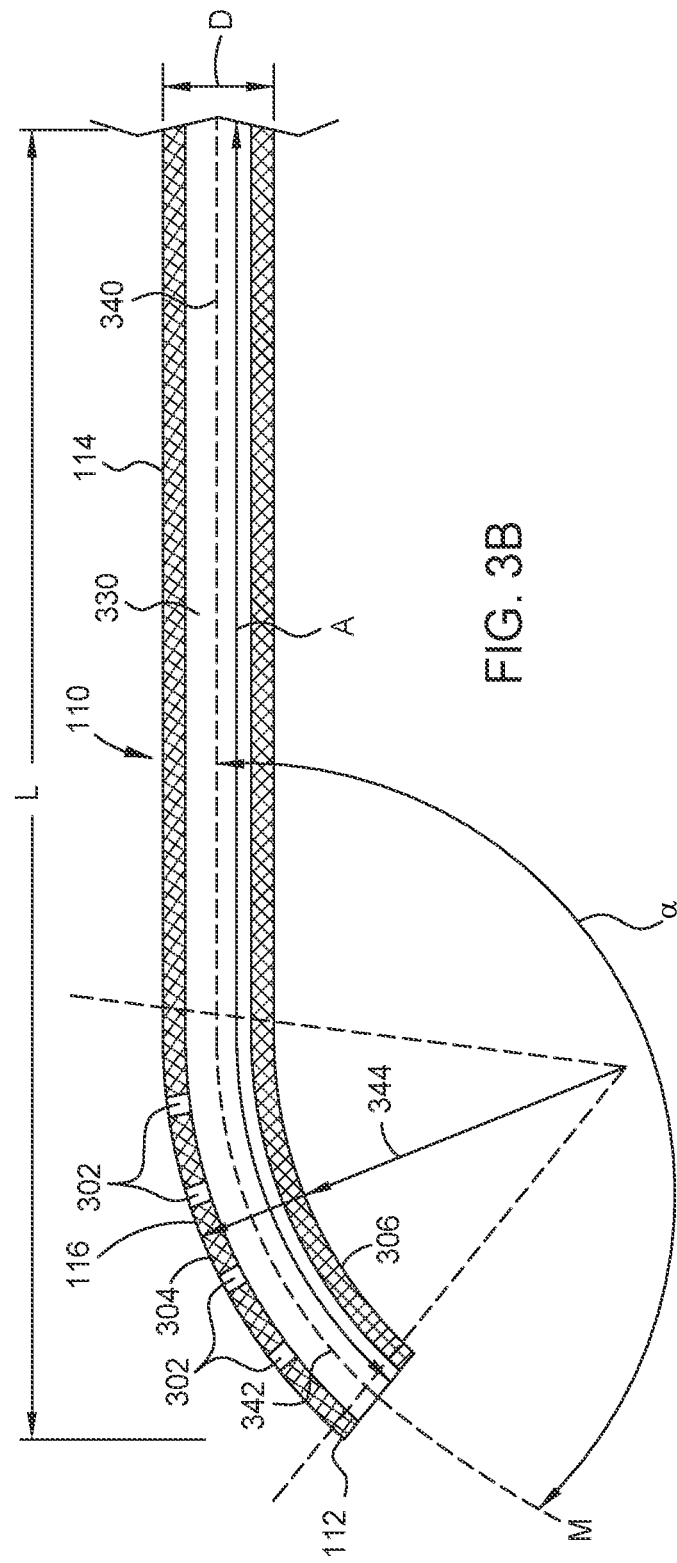

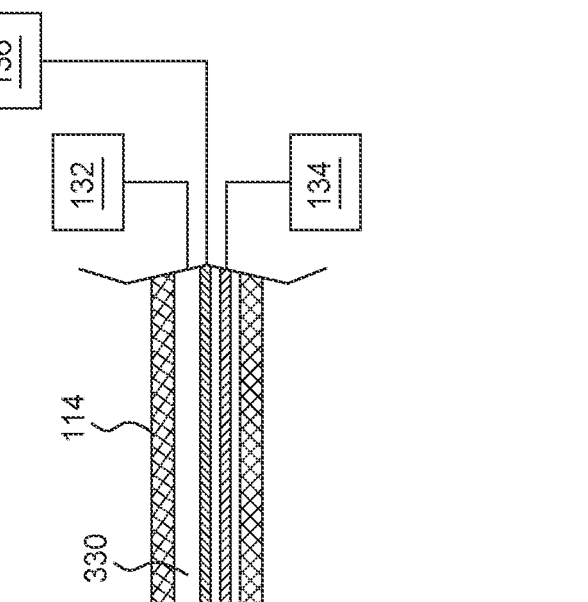
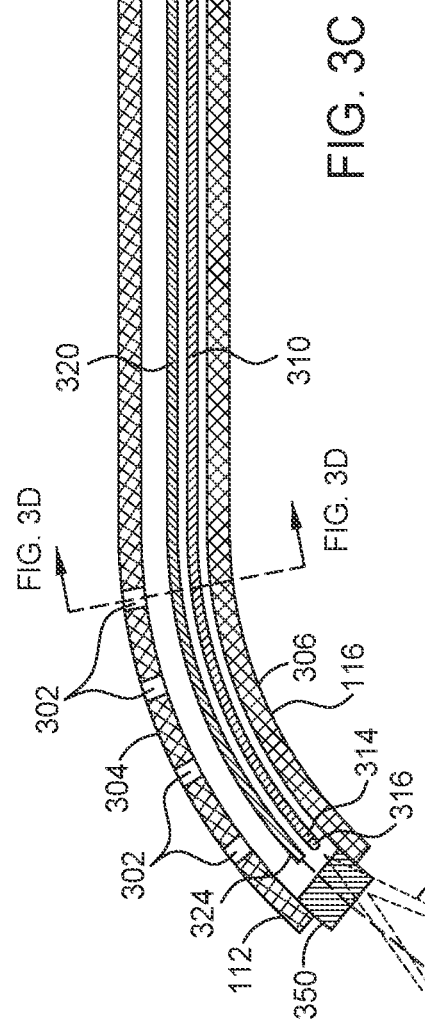
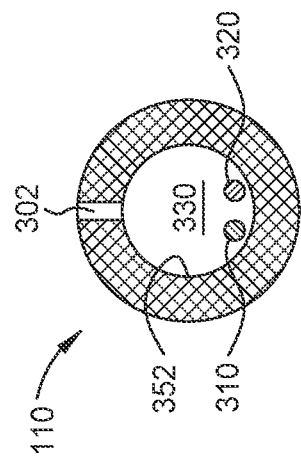

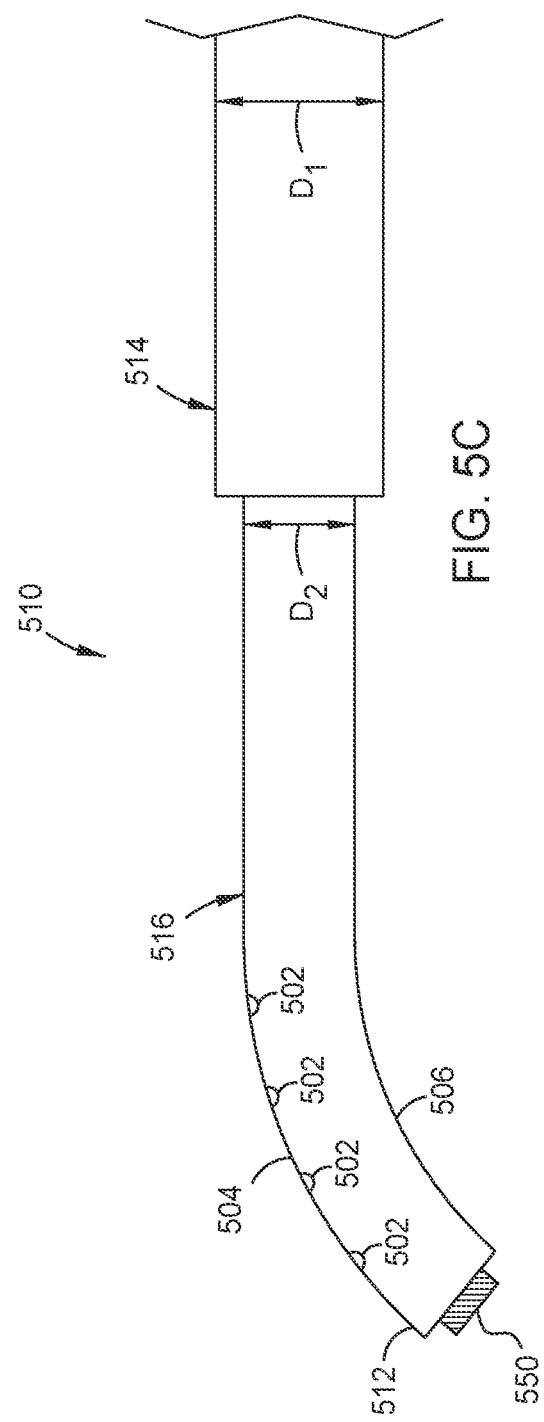

VITREORETINAL INSTRUMENTS FOR ILLUMINATION, FLUID ASPIRATION, AND PHOTOCOAGULATION

PRIORITY CLAIM

This application claims the benefit of priority of U.S. Provisional Patent Application Ser. No. 63/230,138 titled "VITREORETINAL INSTRUMENTS FOR ILLUMINATION, FLUID ASPIRATION, AND PHOTOCOAGULATION," filed on Aug. 6, 2021, whose inventor is Steven T. Charles, which is hereby incorporated by reference in its entirety as though fully and completely set forth herein.

BACKGROUND

In a healthy human eye, the retina is physically attached to the choroid via the retinal pigment epithelium ("RPE") in a generally circumferential, e.g., hemi-spherical, manner behind the pars plana. The vitreous humor, a transparent jelly-like material that fills the posterior segment of the eye, helps to cause the remainder of the retina to lie against, but not physically attach to, the choroid.

Sometimes a portion of the retina may break or tear and detach from the RPE. In certain examples, retinal detachment allows liquid vitreous humor and sometimes, aqueous humor, to flow between the retina and the RPE, creating a build-up of subretinal fluid. Either condition may result in a loss of vision for the patient.

During surgical repair or reattachment of the retina, a surgeon may insert a vitreoretinal instrument into the posterior segment of the eye via a sclerotomy, which is an incision through the sclera at the pars plana. The surgeon may also insert an endoilluminator and an infusion cannula into the eye via similar incisions, and may sometimes substitute an aspiration probe for the vitreoretinal instrument. While viewing the posterior segment under a microscope and with the aid of the endoilluminator, the surgeon may cut and aspirate away vitreous humor using the vitreoretinal instrument to gain access to the retinal detachment or tear. During this portion of the procedure, a saline solution may be infused into the eye via the infusion cannula to maintain the appropriate intraocular pressure.

Next, the surgeon may remove fluid from under the retina and inject air, an air-gas mixture, or a perfluorocarbon to re-approximate the detached portion of the retina in the proper location and flatten the retina against the RPE or choroid. A soft tip cannula, forceps, or other tool may be utilized for such manipulation. In certain cases, a perfluorocarbon liquid is injected into the posterior segment of the eye as a retinal tamponade while saline solution is displaced and removed therefrom, a procedure which may be referred to as "fluid/perfluorocarbon exchange." In certain cases, air is injected as a retinal tamponade fluid while the saline solution is aspirated, a procedure which may be referred to as "fluid/air exchange." In certain other cases, a mixture of air and gas, such as $SF_6$, $C_3F_8$, or $C_2F_6$, is injected as a retinal tamponade fluid while the saline solution is aspirated, a procedure which may be referred to as "fluid/gas exchange." As used herein, a "fluid" may include any liquid or gas that is suitable for use in the eye, including, but not limited to, saline solution with or without additives, silicone oil, a perfluorocarbon liquid, air, or a perfluorocarbon gas.

After performing one of the above-described exchanges, the surgeon may drain, e.g., aspirate via a suitable cannula, metal cannula, or soft tip cannula, any subretinal fluid present between the retina and the choroid through the retinal break or a drainage retinotomy, and thereafter use a laser probe to repair or reattach the retina via endophotocoagulation. To effect the repair, the retina must be placed against the RPE or choroid so that the RPE will absorb laser energy from the laser probe. The presence of subretinal fluid between the retina and the choroid may prevent laser uptake during repair of the retina, leading to inefficiencies during such procedures. Accordingly, it is advantageous to drain subretinal fluid from the surgical site, via an aspiration probe, before endophotocoagulation with a laser probe.

In certain cases, after the initial drainage of subretinal fluid, subretinal fluid may re-accumulate at the surgical site due to posterior flow, thereby requiring additional drainage. When using a conventional aspiration probe and laser probe, the aspiration probe must be either maintained within the posterior segment of the eye during endophotocoagulation, which would require a chandelier for illumination, or be re-inserted through the same or a new incision as the laser probe. However, repeated removal and insertion to exchange the aspiration probe and laser probe may cause unnecessary trauma to the eye at the incision site, retina or lens bump during tool exchange, and/or procedural delay during the retinal repair.

SUMMARY

According to certain embodiments, an instrument for removing subretinal fluid from an eye is provided. The instrument comprises: a handle; a cannula coupled to the handle, a distal portion of the cannula having a curvature corresponding to a curvature of a retina of the eye, the cannula further comprising: a lumen extending through the cannula; and at least one port adjacent to a distal end of the cannula for aspirating subretinal fluid from the eye into the lumen; a first optical fiber extending through the cannula for propagating an illumination light through the distal end of the cannula; and a second optical fiber extending through the cannula for propagating a laser light through the distal end of the cannula.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3A illustrates an enlarged side view of the cannula of the surgical instrument of FIG. 1, in accordance with certain embodiments of the present disclosure.

FIG. 3B illustrates an enlarged, cross-sectional side view of the cannula of the surgical instrument of FIG. 1, in accordance with certain embodiments of the present disclosure.

FIG. 3C illustrates an enlarged, cross-sectional side view of the cannula of the surgical instrument of FIG. 1, in accordance with certain embodiments of the present disclosure.

FIG. 3D illustrates an enlarged, cross-sectional front view of the cannula of the surgical instrument of FIG. 1, in accordance with certain embodiments of the present disclosure.

FIG. 5C illustrates an enlarged side view of the cannula of the surgical instrument of FIGS. 5A-5B, in accordance with certain embodiments of the present disclosure.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body.

As used herein, the term "about" may refer to a +/−10% variation from the nominal value. It is to be understood that such a variation can be included in any value provided herein.

The present disclosure relates generally to small-gauge instrumentation (e.g., 23, 25, or 27 gauge) for surgical procedures, and more specifically, to vitreoretinal instruments for retinal repair and reattachment procedures, as well as associated methods of use. Certain embodiments of the present disclosure provide a curved or articulating probe configured to provide illumination, fluid aspiration, and endophotocoagulation. Accordingly, the probe enables aspiration of subretinal fluid that re-accumulates after initial drainage and during endophotocoagulation without the need to exchange surgical instruments or insert an additional instrument into the intraocular space. Furthermore, the combined functionalities of the probe enable a surgeon to simultaneously perform scleral depression with the surgeon's other hand while aspirating fluid and/or performing retinal endophotocoagulation. As a result, utilization of the aforementioned probe enables improved procedural efficiency and reduced risk of injury to the patient's eye.

Figure 1:
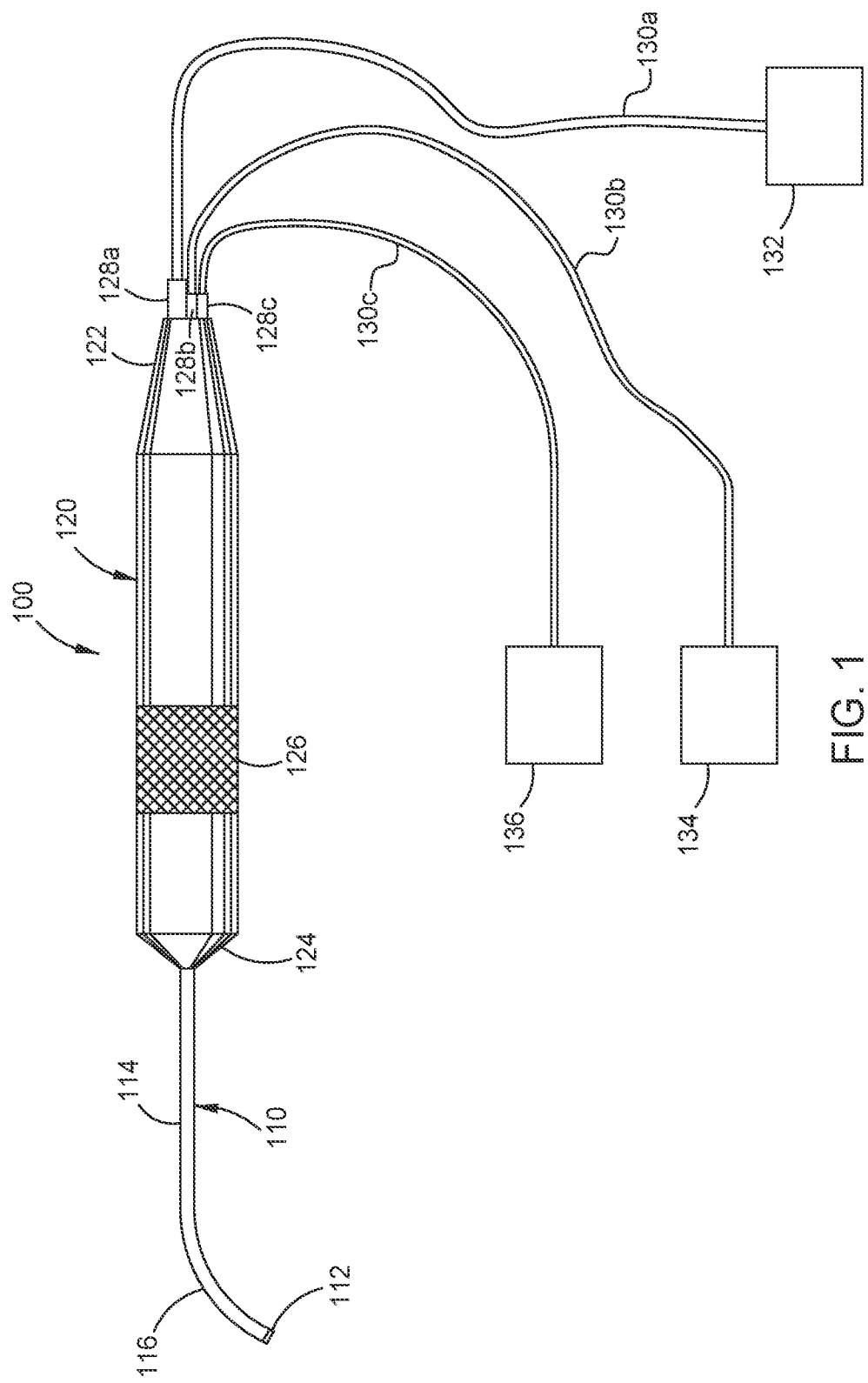
FIG. 1 illustrates an example surgical instrument, in accordance with certain embodiments of the present disclosure.
Figure 2:
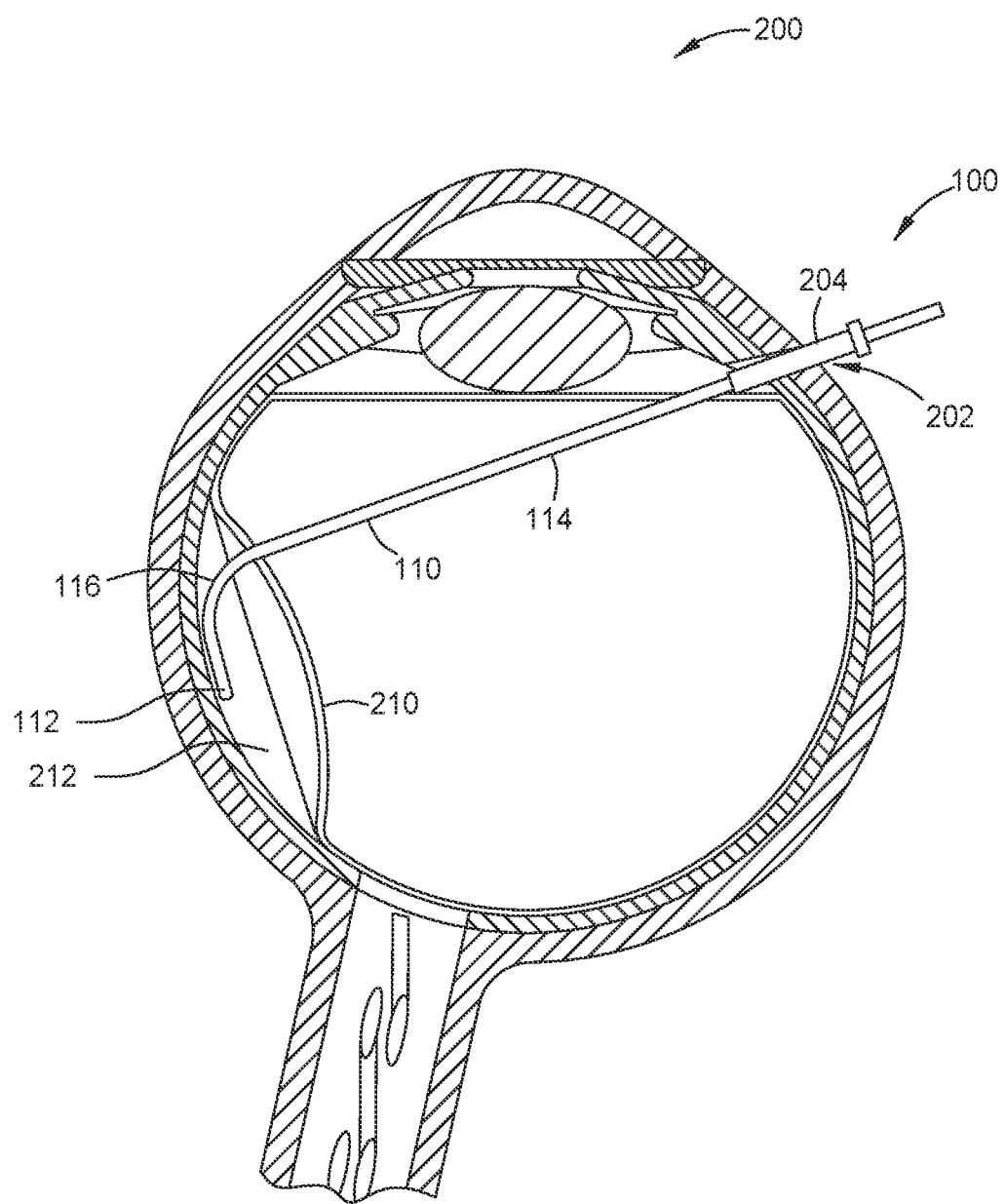
FIG. 2 illustrates a cross-sectional view of an eye in which an example cannula of the surgical instrument of FIG. 1 is inserted, in accordance with certain embodiments of the present disclosure.

FIG. 1 illustrates example surgical instrument 100, according to certain embodiments. Surgical instrument 100 may include flexible cannula 110. As illustrated in FIG. 2, during an ophthalmic surgical procedure, cannula 110 may be positioned within eye 200 through incision 202, known as a sclerotomy, by way of access cannula 204, which is a component separate from cannula 110. While present in eye 200, cannula 110 may be used to illuminate the intraocular space within eye 200 via one or more optical fibers disposed within cannula 110, aspirate materials from eye 200 via one or more aspiration ports disposed through cannula 110, and propagate a laser beam for endophotocoagulation of tissues within eye 200 via the one or more optical fibers. In certain examples, during a vitreoretinal surgical procedure, distal end 112 of cannula 110 may be inserted into eye 200 behind retina 210 to illuminate subretinal space 212, drain subretinal fluid therefrom, and thereafter seal retina 210 via photocoagulation.

Referring again to FIG. 1, surgical instrument 100 may also include handle 120 having proximal end 122 and distal end 124. In certain embodiments, handle 120 is a hand piece having an outer surface configured to be held by a user, e.g., a surgeon. As such, handle 120 may be ergonomically contoured to substantially fit the hand of the user. In certain embodiments, the outer surface may be textured or have one or more gripping features 126 formed thereon, such as one or more grooves and/or ridges. Handle 120 may be made from any material commonly used for such instruments and suitable for ophthalmic surgery. For example, handle 120 may be formed of lightweight aluminum, a metal alloy, a polymer, or other suitable material. In certain embodiments, handle 120 may be sterilized and used in more than one surgical procedure, or may be a single-use device.

Handle 120 further includes a plurality of ports 128 (e.g., three ports 128a-c are depicted in FIG. 1) at proximal end 122 for connection with a plurality of tubes 130 (e.g., three tubes 130a-c are depicted in FIG. 1). In the example of FIG. 1, port 128a provides a fluid connection between an interior lumen of handle 120 and cannula 110 (described below) and tube 130a, which may be an extruded tube for fluid coupling of surgical instrument 100 to a vacuum source 132 of a surgical console for aspiration of e.g., subretinal fluid from eye 200. In certain embodiments, port 128a includes a Luer Lok-type connector for coupling handle 120 to tube 130a. Port 128b provides a connection for tube 130b, which may be an optical fiber cable for coupling an optical fiber within handle 120 and cannula 110 to an illumination light source 134 of a surgical console for propagation of illumination light to eye 200. Port 128c provides connection for 130c, which may be an optical fiber cable for coupling an optical fiber within handle 120 and cannula 110 to a laser light source 136 of a surgical console for propagation of laser light to eye 200. While using surgical instrument 100, a user may activate any one of vacuum source 132, illumination light source 134, and laser light source 136 via one or more toggles (e.g., buttons, switches, etc.) on handle 120, a surgical console in communication with surgical instrument 100, or a foot pedal in communication with a surgical console and/or surgical instrument 100.

Note that in the example of FIG. 1, illumination light source 134 and laser light source 136 are shown as distinct light sources which may each couple to a separate optical fiber (e.g., one optical fiber for propagating illumination light and another optical fiber for propagating laser light). In such embodiments, each optical fiber may be sheathed within a separate optical fiber cable, e.g., tube 130b and 130c. In other embodiments, however, a single light source and a single optical fiber may be utilized to generate and propagate, respectively, both illumination light and laser light, which further only requires a single optical fiber cable, e.g., tube 130b or 130c.

Cannula 110 extends axially from distal end 124 of handle 120 and may be directly or indirectly coupled to handle 120 within an interior chamber thereof. Generally, cannula 110 is formed of a flexible or elastic material such as, e.g., a superelastic or shape memory alloy, which may still have enough rigidity to facilitate manipulation of ocular tissues during a surgical procedure. Examples of suitable superelastic alloys include nickel titanium (i.e., nitinol (Nickel Titanium Naval Ordinance Laboratory)) and spring steel. However, other flexible metals are also contemplated. In certain embodiments, cannula 110 includes a proximal, straight portion 114 and a distal, curved portion 116. With reference to FIG. 2, when curved portion 116 is disposed in or otherwise passes through access cannula 204, curved portion 116, due to being made of a superelastic material, flexes or straightens to allow passage thereof through access cannula 204.

FIG. 3A illustrates an enlarged side view of cannula 110, and FIG. 3B illustrates a stylized, cross-sectional side view of cannula 110. As shown, cannula 110 is generally an elongated tubular member including straight portion 114 and curved portion 116. Longitudinal axis M, shown in FIG. 3B, extends axially through cannula 110 and includes first portion 340 through straight portion 114 and second portion 342 through curved portion 116. In certain embodiments, cannula 110 has an axial length A (e.g., along axis M) between about 15 mm (millimeters) and about 45 mm, but may have a longer or shorter axial length A in some embodiments. In further embodiments, cannula 110 has a linear length L shorter than axial length A due to the curvature of curved portion 116, such as a linear length L between about 15 mm and about 30 mm, but may have a longer or shorter linear length L in some embodiments.

Cannula 110 may generally have an outer diameter D less than about 20 gauge, such as an outer diameter D of less than about 23 gauge, 25, gauge, 27 gauge, or 29 gauge. In certain embodiments, as shown in FIGS. 3A-3B, cannula 110 may have a constant or uniform outer diameter D along axis M, while in other embodiments, cannula 110 may have a non-uniform outer diameter D along axis M. For example, in certain embodiments, cannula 110 may have a tapered outer diameter D along axis M, wherein outer diameter D decreases distally along axis M. In other embodiments, cannula 110 is segmented along axis M, wherein different segments of cannula 110 may have different outer diameters D. For example, a more distal segment of cannula 110 may have a smaller diameter D than a more proximal segment of cannula 110.

Curved portion 116 of cannula 110 is disposed distally relative to straight portion 114 and is defined by outer curved surface 304 and inner curved surface 306. In certain embodiments, curved portion 116, or at least inner curved surface 306, has a radius of curvature similar to that of the retina of a patient's eye, e.g., retina 210 in FIG. 2. For example, as shown in FIG. 3B, longitudinal axis M of cannula 110, or inner curved surface 306, may have a curvature defined by a radius 344 matching or corresponding to a radius of the curvature of retina 210. As further illustrated in FIG. 3B, curved portion 116 may curve so as to define angle α between portions 340 and 342 of axis M. In certain embodiments, angle α is within a range of about 90° and about 180°, such as between about 110° and about 160°, such as between about 120° and about 150°, such as between about 120° and about 140°.

Curved portion 116 further includes one or more aspiration ports 302 disposed along an outer curved surface 304 thereof that may be fluidly coupled to, e.g., vacuum source 132 via an interior lumen 330. Lumen 330 serves as an aspiration channel through cannula 110 to an interior chamber of handle 120, as well as to tube 130a shown in FIG. 1. Thus, upon activation of vacuum source 132, ocular materials within, e.g., eye 200 may be aspirated through aspiration ports 302, into lumen 330 of cannula 110, and through tube 130a. By placing aspiration ports 302 along outer curved surface 304, the risk of incarcerating the retina during subretinal fluid drainage with surgical instrument 100 is reduced, because, when inserted through a tear in the retina, e.g., the retina is located proximate to inner curved surface 306 and opposite outer curved surface 304. Generally, aspiration ports 302 may have any suitable morphology for aspirating e.g., subretinal fluid, and may further be disposed in any suitable arrangement along outer curved surface 304. For example, aspiration ports 302 may be disposed in one or more longitudinal rows along curved surface 304, as depicted in FIGS. 3A-3C. Due to the curvature of curved portion 116, aspiration ports 302 may be angularly and laterally offset from straight portion 114 of cannula 110.

As described above, surgical instrument 100 is configured to propagate and deliver both illumination light and laser light to eye 200 via one or more optical fibers disposed within cannula 110. FIGS. 3C-3D illustrate an example of cannula 110 in an assembled surgical instrument 100 having two optical fibers disposed therein, wherein each optical fiber is configured to propagate either illumination light or laser light. Note that although the examples of FIGS. 3C-3D are described as having two optical fibers, a single optical fiber configured to propagate both illumination light and laser light may also be utilized in certain embodiments.

FIG. 3C illustrates a stylized, cross-sectional longitudinal view of cannula 110 having first optical fiber 310 and second optical fiber 320 housed therein. As depicted, cannula 110 includes lumen 330, which in addition to providing an aspiration channel for ocular materials, e.g., subretinal fluid, also provides a conduit for running first and second optical fibers 310, 320 through cannula 110 to distal end 112. Distal end 112 of cannula 110 further includes protective window 350, which provides an optically clear or transparent barrier through which laser light and/or illumination light may be transmitted during a surgical procedure. Accordingly, window 350 comprises an optically clear or transparent material, such as sapphire, fused silica, or other glass or ceramics materials with high transition temperatures. In certain aspects, the transparent material has optical power and, in certain other aspects, the transparent material does not have optical power. Optical power (also referred to as dioptric power, refractive power, focusing power, or convergence power) is the degree to which a lens, mirror, or other optical system converges or diverges light. Accordingly, window 350 may itself be a lens, such as a spherical lens having concave or convex surfaces, or a nonspherical lens.

First optical fiber 310 may be designed to operate as an optical waveguide and propagate illumination light 312 produced by illumination light source 134 (e.g., a light engine) through distal end 112 of cannula 110 to illuminate a surgical site within an intraocular space, e.g., a site or retinal tear or detachment. In certain embodiments, first optical fiber 310 is an optical nanofiber having a diameter less than about 30 μm (micrometers), such as a diameter between about 20 μm and about 30 μm. In such embodiments, the reduced overall cross-sectional footprint (i.e., area occupied) of first optical fiber 310 increases the amount of unoccupied cross-sectional area within lumen 330, thereby providing a wider fluid flowpath and improving flow of aspirated ocular materials through lumen 330. Further, an optical nanofiber may have a reduced stiffness as compared to larger, more conventional optical fiber, thus enabling relatively greater flexibility (e.g., bending over a greater range of angles) of cannula 110.

As depicted in FIG. 3C, first optical fiber 310 may further include microlens 316 disposed at terminal end 314 thereof to produce a divergent, widespread illumination beam. Accordingly, microlens 316 may be a spherical lens (e.g., ball lens) having concave or convex surfaces, or a non-spherical lens (e.g., bullet lens). In certain embodiments, terminal end 314 abuts window 350 within lumen 330, while in other embodiments, as depicted in FIG. 3C, terminal end 314 is spaced apart from window 350.

In certain embodiments, illumination light source 134 may be used to provide illumination light 312 to first optical fiber 310 in a continuous or pulsed manner, which may then be propagated by first optical fiber 310 through distal end 112 of cannula 110 in one of a variety of ways. Illumination light source 134 may be any suitable type of light source, such as a light emitting diode (LED)-based light source or a superluminescent diode (SLED)-based light source. However, other types of light sources are further contemplated, such as xenon- or halogen-based light sources, UV (Ultraviolet) light sources, white light sources, etc. As described above, illumination light source 134 may be part of an illumination module within a surgical console, or may be a separate, standalone light engine.

Similar to first optical fiber 310, second optical fiber 320 may be designed to operate as an optical waveguide and propagate laser light 322 produced by laser light source 136 (e.g., a laser engine) through distal end 112 of cannula 110 to repair retinal tissue (labeled 210 in FIG. 2) within eye 200 via endophotocoagulation. In certain embodiments, terminal end 324 of second optical fiber 320 abuts window 350 within lumen 330, while in other embodiments, as depicted in FIG. 3C, terminal end 314 is spaced apart from window 350. In certain embodiments, second optical fiber 320 may be an optical nanofiber having a diameter less than about 30 μm, such as a diameter between about 20 μm and about 30 μm. As described above, in such embodiments, the reduced overall cross-sectional of optical fiber 320 may facilitate a wider fluid flowpath through cannula 110 and improve flow of aspirated ocular materials through lumen 330. Additionally, the reduced stiffness of a nanofiber may enable relatively greater flexibility of cannula 110 as compared to a larger, more conventional optical fiber.

The characteristics of laser light 322 propagated through second optical fiber 320 are such that laser light 322 coagulates retinal tissue within the path of laser light 322 via thermal energy, which then heals to seal the retina 210. Burning is effected by laser light 322 heating the tissue to a temperature above 50° C. (degrees Celsius) but below 100° C., at which point proteins in the tissue denature and thrombocytes initiate coagulation. Accordingly, laser light source 136 may include any suitable type of ophthalmic laser light source for producing a photocoagulation laser light capable of treating retinal tissue (e.g., for performing retinopexy). For example, laser light source 136 may be configured to produce a laser light having a wavelength between about 440 nm (nanometers) and about 830 nm, such as a blue-green laser light source (e.g., 488 nm), a green laser light source (e.g., 514 nm), a high power green diode laser light source, or a red laser light source (e.g., 647 nm). In certain embodiments, laser light source 136 is an Nd:YAG laser light source (e.g., 532 nm) or a frequency-doubled CW Nd:YAG laser light source (e.g., 1064 nm). In certain embodiments, laser light source 136 produces laser light 322 having a pulse rate within a range of about 1 kilohertz (kHz) and about 500 kHz, which can effectively provide heating of the retina, though other pulse rate ranges are contemplated as well. In certain embodiments, laser light source 136 produces a continuous-wave laser light 322. For example, laser light source 136 may produce a continuous-wave laser light 322 at low power.

FIG. 3D illustrates a sectional front view of cannula 110 with first optical fiber 310 and second optical fiber 320 housed therein, in accordance with certain embodiments of the present disclosure. As shown, first optical fiber 310 and second optical fiber 320 are disposed along (e.g., coupled to) a longitudinal portion of interior sidewall 352 of cannula 110, side-by-side and opposite of aspiration ports 302. Optical fibers 310, 320 may be coupled or bonded to interior sidewall 352 via any suitable adhesive or bonding mechanism. For example, in certain embodiments, optical fibers 310, 320 may be bonded to interior sidewall 352 with an epoxy or acrylic adhesive. However, other suitable adhesives or binders are also contemplated. Coupling both optical fibers 310, 320 to interior sidewall 352 and opposite of aspiration ports 302 may improve flow of ocular materials aspirated through aspiration ports 302 and lumen 330 by reducing the amount of flowpath obstruction at a central portion of lumen 330 and/or near aspiration ports 302.

Figure 4:
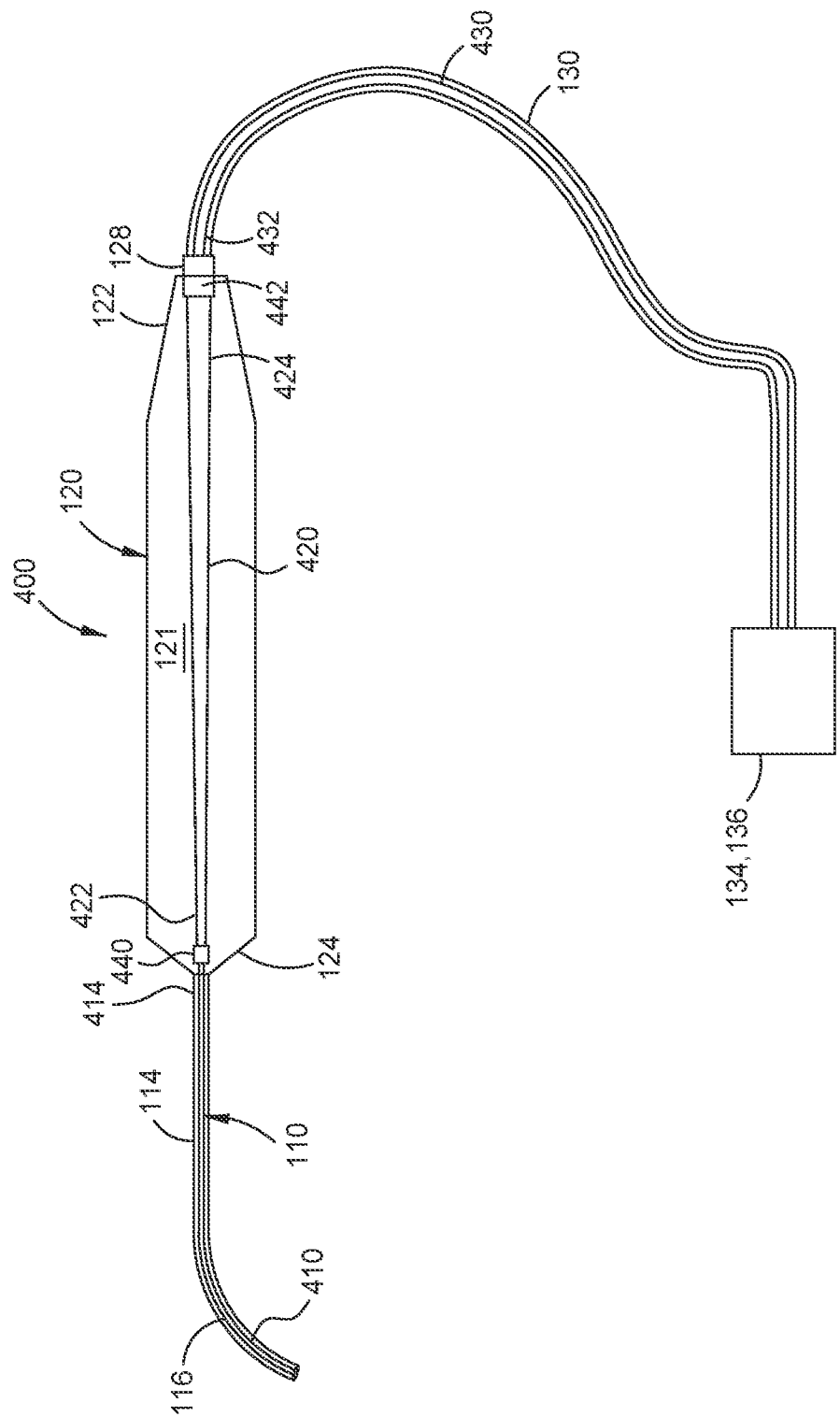
FIG. 4 illustrates a schematic cross-sectional side view of the surgical instrument of FIG. 1, in accordance with certain embodiments of the present disclosure.

FIG. 4 illustrates a schematic, cross-sectional side view of surgical instrument 400, in accordance with certain embodiments of the present disclosure. More particularly, FIG. 4 depicts an example arrangement of optical fibers disposed within and coupled to surgical instrument 400, which is representative of certain embodiments described herein utilizing optical nanofibers, e.g., optical fibers having a diameter of about 30 μm or less, within cannula 110.

As shown in FIG. 4, surgical instrument 400 includes optical nanofiber 410 extending through cannula 110. Optical nanofiber 410 is representative of first optical fiber 310 and/or second optical fiber 320 in FIGS. 3C-3D, wherein optical fibers 310 and/or 320 are optical nanofibers. Note that although only one optical nanofiber 410 is depicted, the present arrangement may apply to both first optical fiber 310 and second optical fiber 320. As described above, utilization of optical nanofiber 410 increases the unoccupied cross-sectional area within lumen 330 for improved aspiration of ocular materials by surgical instrument 400. However, conventional surgical consoles and/or illumination or laser light sources may only be compatible with standard 84-inch-long optical fibers having larger diameters of about, e.g., 120 μm. Therefore, in order to enable compatibility of surgical instrument 400 with conventional surgical consoles and/or illumination and laser light sources, optical nanofiber 410 may be optically coupled to a surgical console and/or illumination or laser light sources via one or more additional optical fibers joined (i.e., mated) in series.

In the arrangement of FIG. 4, optical nanofiber 410 is proximally joined to tapered optical fiber 420 at junction 440 within lumen 421 of handle 120, and tapered optical fiber 420 is proximally joined to delivery fiber 430 at junction 442 within lumen 421. Tapered optical fiber 420 generally has a tapered (e.g., non-constant) diameter that increases proximally to enable optical coupling of optical nanofiber 410 with delivery fiber 430, which may be a standard-sized optical fiber. Accordingly, tapered optical fiber 420 includes a smaller, distal end 422 configured to mate with proximal end 414 of optical nanofiber 410, as well as a larger, proximal end 424 configured to mate with distal end 432 of delivery fiber 430. Delivery fiber 430 is at least partially disposed within tube 130, which may be an optical fiber cable extending through port 128 of handle 120 for physical coupling of surgical instrument 400 to a surgical console and/or illumination or laser light source, such as illumination light source 134 or laser light source 136.

In certain embodiments, optical nanofiber 410 and tapered optical fiber 420, and/or tapered optical fiber 420 and delivery fiber 430 are butt-joined at junctions 440, 442 via fusion splicing or mechanical splicing. For example, in certain embodiments, optical nanofiber 410 and tapered optical fiber 420, and/or tapered optical fiber 420 and delivery fiber 430, are mechanically spliced using an epoxy or mechanical clamping mechanism at junctions 440, 442. In further embodiments, a connector, such as a straight mating sleeve or a tapered/biconical mating sleeve, is utilized to butt-join optical nanofiber 410 and tapered optical fiber 420 at junction 440, and/or tapered optical fiber 420 and delivery fiber 430 at junction 442.

In certain embodiments, optical nanofiber 410 has a numerical aperture (NA) of about 0.66, a critical angle of about 41.3°, and a launch cone angle of 82.6°. In certain other embodiments, optical nanofiber 410 has a numerical aperture (NA) of about 0.86, a critical angle of about 59.32°, and a launch cone angle of 118.6°. To optimize coupling efficiency between optical nanofiber 410 and tapered optical fiber 420, and/or tapered optical fiber 420 and delivery fiber 430, which may otherwise be negatively affected as a result of variations in core diameters, NA, refractive-index profiles, etc., tapered optical fiber 420 can be selected based on the optical characteristics of optical nanofiber 410, and delivery fiber 430 can be selected based on the optical characteristics of tapered optical fiber 420. For example, based on the characteristics of optical nanofiber 410 described above (e.g., NA, critical angle, launch cone angle, etc.), a selected delivery fiber 430 may have a lower NA but larger diameter.

In certain embodiments, tapered optical fiber 420 and/or delivery fiber 430 may be selected based on the following formula:

$$A*\Omega \text{ (proximal end of smaller fiber)} = A*\Omega \text{ (distal end of larger fiber)},$$

wherein "A" is a cross-sectional area of the corresponding fiber end, and "Ω" is the solid angle of the corresponding fiber end's light cone. Thus, in order to optimize coupling efficiency between, e.g., optical nanofiber 410 and tapered optical fiber 420, the $A*\Omega$ product of optical nanofiber 410 may be matched to the $A*\Omega$ product of distal end 422 of tapered optical fiber 420. In certain embodiments, selecting tapered optical fiber 420 and subsequently, delivery fiber 430, based on optical characteristics of optical nanofiber 410 may provide the additional benefit of moving any coupling losses away from cannula 110 and/or handle 120, which may otherwise result in increased and undesired heat formation therein.

Figure 5A:
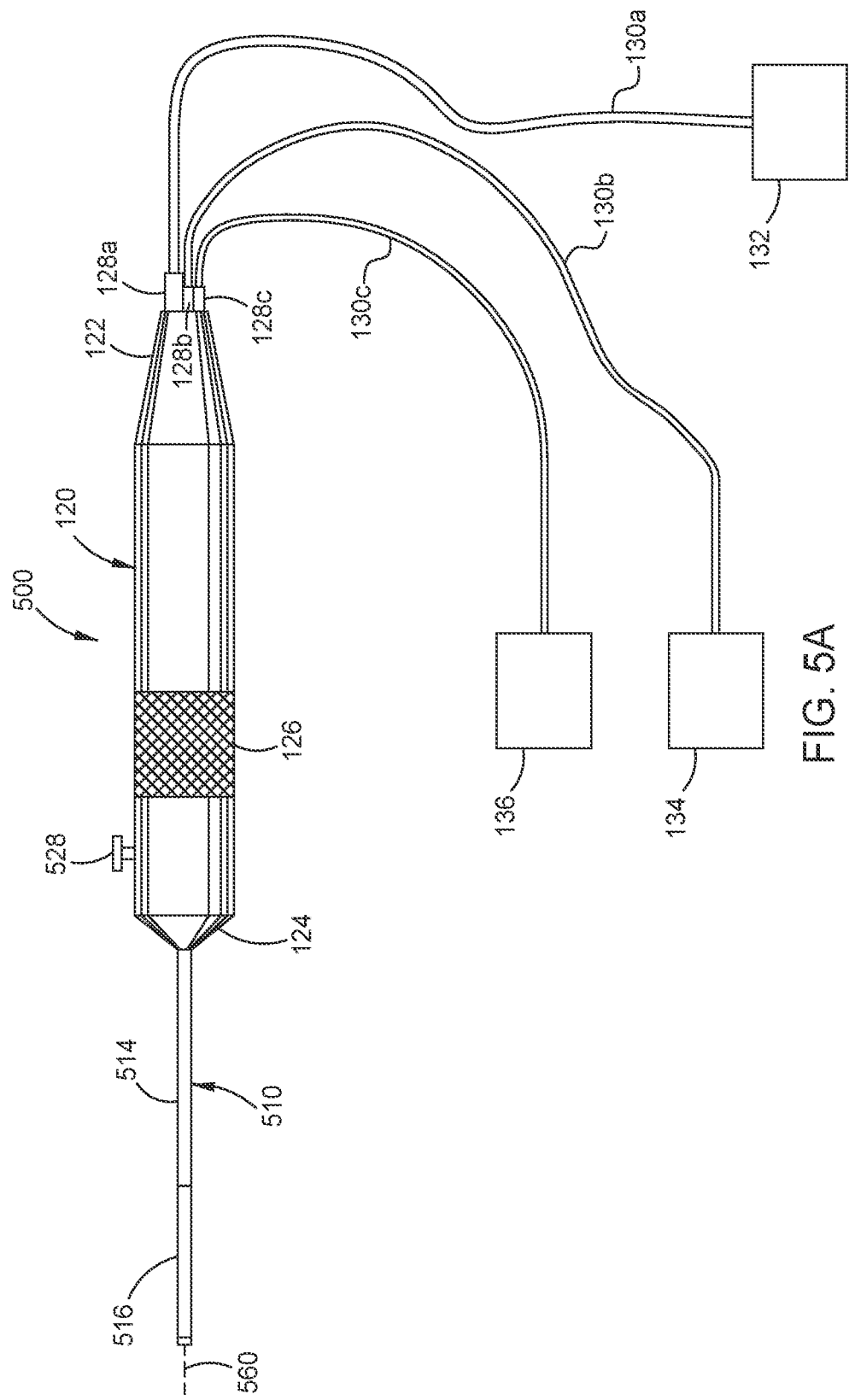
FIGS. 5A-5B illustrate different configurations of another example surgical instrument, in accordance with certain embodiments of the present disclosure.
Figure 5B:
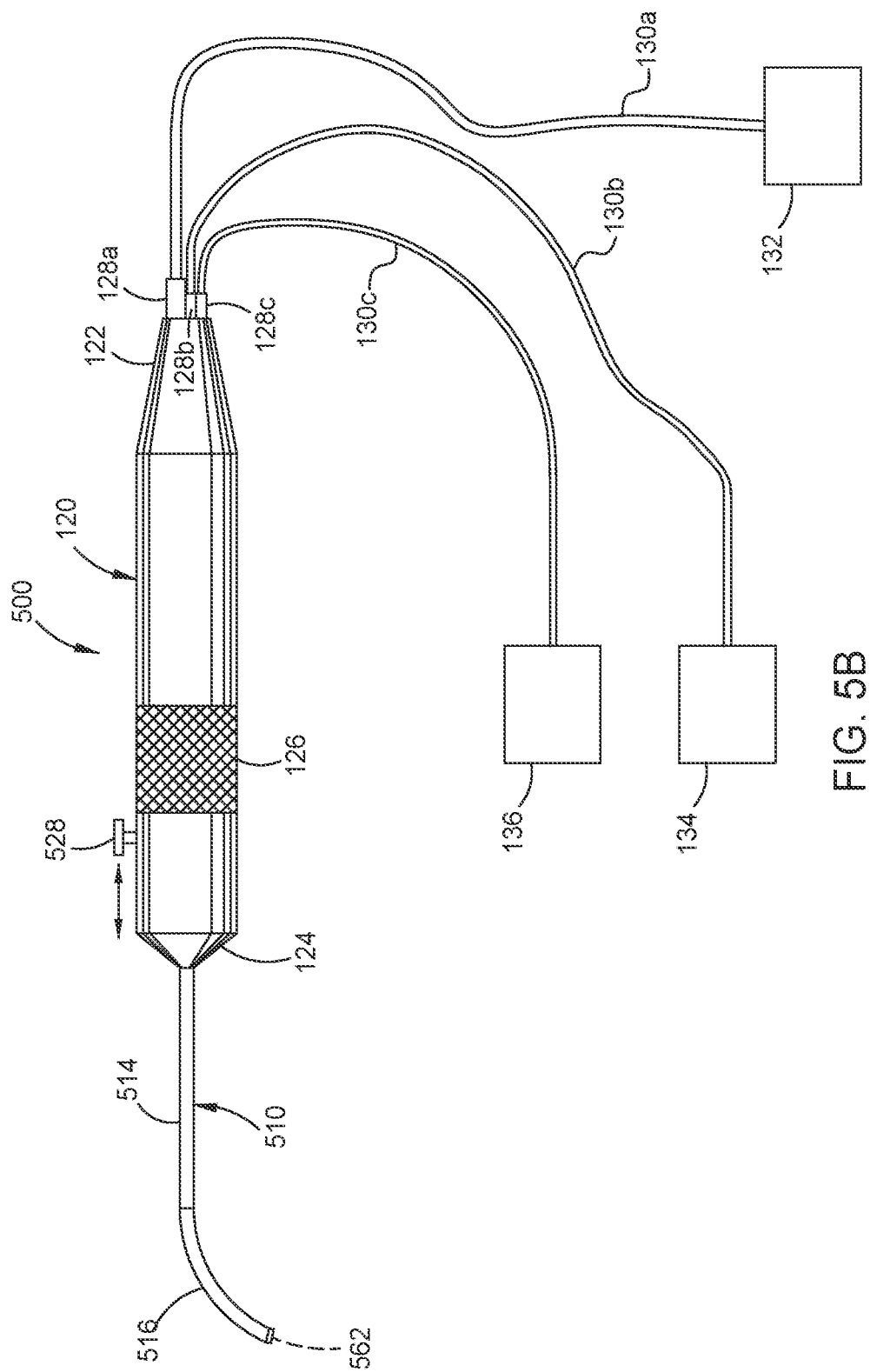

FIGS. 5A-5B schematically illustrate different configurations of another example surgical instrument 500, and FIG. 5C illustrates an enlarged side view of cannula 510 of surgical instrument 500, in accordance with certain embodiments of the present disclosure. Surgical instrument 500 is substantially similar to surgical instruments 100, 400 described above, but includes cannula 510 with articulating distal tip 516. Thus, in addition to the advantages provided by the combined functions of illumination, aspiration, and endophotocoagulation, surgical instrument 500 further provides a degree of controllable articulation in one or more selected directions.

As shown, in addition to articulating distal tip 516, cannula 510 includes proximal portion 514, which extends axially from distal end 124 of handle 120 and may be directly or indirectly coupled to handle 120. Proximal portion 514 may generally have outer diameter $D_1$ less than about 20 gauge, such as outer diameter $D_1$ (shown in FIG. 5C) of less than about 23 gauge, 25, gauge, 27 gauge, or 29 gauge. In certain embodiments, proximal portion 514 is formed of a rigid and biocompatible material, such as stainless steel or other suitable rigid metal alloy. In contrast, distal tip 516 may be formed of a flexible or elastic material such as, e.g., a superelastic or shape memory alloy, which may still have enough rigidity to facilitate manipulation of ocular tissues during a surgical procedure. Examples of suitable superelastic alloys include nitinol and spring steel. However, other flexible metals for distal tip 516 are also contemplated. In certain embodiments, distal tip 516 has outer diameter $D_2$, which is substantially the same or less than outer diameter $D_1$ of proximal portion 514. For example, in certain embodiments, distal tip 516 has outer diameter $D_2$ of less than about 20 gauge, 23 gauge, 25, gauge, 27 gauge, or 29 gauge.

Distal tip 516 may articulate in a selected direction in a controllable manner by applying tension to a control mechanism secured within cannula 510. In certain embodiments, the control mechanism includes a pull-wire or similar device extending through distal tip 516 and proximal portion 514, which may be controlled by applying tension thereto via toggle 528, such as a button, pinion, sliding pin, lever, etc., on handle 120. In certain embodiments, distal tip 516 may be articulated between straight position 560, shown in FIG. 5A, and curved position 562, shown in FIG. 5B. In certain embodiments, when distal tip 516 is in curved position 562, distal tip 516 may have a radius of curvature matching or similar to that of the retina of a patient's eye, e.g., retina 210 in FIG. 2. Accordingly, when disposed in curved position 562, distal tip 516 may be inserted through a tear in the retina, e.g., retina 210, to access the subretinal space, e.g., subretinal space 212, where the curvature of distal tip 516 substantially conforms with the curvature of the retina for improved aspiration of subretinal fluid with reduced retinal incarceration. Such embodiments provide an advantage over straight and rigid vitreoretinal instruments, with which access to the subretinal space without incarceration of the retina may be difficult, thus limiting such vitreoretinal instruments to a location at a boundary of the retinal break or tear.

Similar to curved portion 116 of cannula 110, distal tip 516 includes one or more aspiration ports 502 (shown in FIG. 5C) disposed through a wall thereof that may fluidly couple to a vacuum source, e.g., vacuum source 132, via an interior lumen of cannula 510, which serves as an aspiration channel through cannula 510 to an interior chamber of handle 120, as well as, e.g., tube 130a. In certain embodiments, aspiration ports 502 are formed along surface 504 that forms an outer curved surface of distal tip 516 when distal tip 516 is in curved position 562. By placing aspiration ports 502 along surface 504, the risk of incarcerating the retina during subretinal fluid drainage with surgical instrument 500 is reduced, because, when inserted through a tear in the retina in curved position 562, e.g., the retina is located proximate to surface 506 and opposite surface 504. Similar to surgical instrument 100, aspiration ports 502 may have any suitable morphology for aspirating e.g., subretinal fluid, and may further be disposed in any suitable arrangement along surface 504. For example, aspiration ports 502 may be disposed in one or more longitudinal rows along surface 504, as depicted in FIG. 5C. When distal tip 516 is in curved position 562, aspiration ports 502 may be angularly and laterally offset from proximal portion 514 of cannula 510.

In addition to providing aspiration, surgical instrument 500 is also configured to propagate and deliver both illumination light and laser light to the eye, e.g., eye 200, via one or more optical fibers disposed within cannula 510. Accordingly, surgical instrument 500 may have the same or substantially similar arrangements of one or more optical fibers therein, as described with reference to surgical instruments 100 and 400 and, therefore, the corresponding details are omitted for brevity. For example, surgical instrument 500 may include two optical fibers disposed therein, wherein each optical fiber is configured to propagate either illumination light or laser light, or surgical instrument 500 may include a single optical fiber, wherein the single optical fiber is configured to propagate both illumination light and laser light. To enable propagation of illumination light and/or laser light from distal tip 516, distal tip 516 may include protective window 550 at distal end 512 thereof, which provides an optically clear or transparent barrier through which laser light and/or illumination light may be transmitted during a surgical procedure. Similar to window 350, window 550 may comprise an optically clear or transparent material, such as sapphire, fused silica, or other glass or ceramics materials with high transition temperatures. In certain aspects, the transparent material may have optical power and, in certain other aspects, the transparent material may not have optical power. Accordingly, window 550 may itself be a lens, such as a spherical lens having concave or convex surfaces, or a nonspherical lens.

As described above, embodiments of the present disclosure provide a curved or articulating probe configured to provide illumination, fluid aspiration, and endophotocoagulation. Accordingly, the probe enables aspiration of subretinal fluid that re-accumulates during endophotocoagulation and after initial drainage due to posterior migration, without the need to exchange surgical instruments multiple times or insert an additional instrument into the intraocular space. Furthermore, the combined functionalities of the probe enable a surgeon to simultaneously perform scleral depression with the surgeon's other hand while aspirating fluid and/or performing retinal endophotocoagulation. As a result, utilization of the aforementioned probe enables improved procedural efficiency and reduced risk of injury to the patient's eye.

Example Embodiments

Embodiment 1: An instrument for removing subretinal fluid from an eye, comprising: a handle; an articulating cannula coupled to the handle, the articulating cannula configurable between a straight configuration and a curved configuration, the articulating cannula comprising: a lumen extending through the cannula; and at least one port adjacent to a distal end of the cannula, the port for aspirating subretinal fluid from the eye into the lumen; a first optical fiber extending through the articulating cannula, the first optical fiber for propagating an illumination light through the distal end of the cannula; and a second optical fiber extending through the articulating cannula, the second optical fiber for propagating a laser light through the distal end of the cannula.

Embodiment 2: The instrument of Embodiment 1 described above, wherein the cannula is formed from a material comprising a superelastic alloy.

Embodiment 3: The instrument of Embodiment 2 described above, wherein the superelastic alloy is nitinol.

Embodiment 4: The instrument of Embodiment 1 described above, wherein a proximal end of the handle comprises a Luer Lok-type connector to connect an extrusion tubing for aspirating the subretinal fluid.

Embodiment 5: The instrument of Embodiment 4 described above, wherein the lumen is in fluid communication with a vacuum source via the extrusion tubing.

Embodiment 6: The instrument of Embodiment 1 described above, wherein the first optical fiber and the second optical fiber are nanofibers have a diameter of about 30 microns or less.

Embodiment 7: The instrument of Embodiment 6 described above, wherein the first optical fiber is joined to a third optical fiber disposed within the handle, the third optical fiber having a tapered diameter from a proximal end thereof to a distal end thereof.

Embodiment 8: The instrument of Embodiment 7 described above, wherein the third optical fiber is joined to a fourth optical fiber at least partially disposed within the handle.

Embodiment 9: The instrument of Embodiment 6 described above, wherein the first optical fiber comprises a microlens at a distal end thereof to produce a divergent beam of illumination light.

Embodiment 10: The instrument of Embodiment 1 described above, wherein the first optical fiber is optically coupled to a light-emitting diode (LED) illumination source.

Embodiment 11: The instrument of Embodiment 1 described above, wherein the first optical fiber is optically coupled to a superluminescent diode (LED) illumination source.

Embodiment 12: The instrument of Embodiment 1 described above, wherein the second optical fiber is optically coupled to a narrowband or broadband laser source.

Embodiment 13: The instrument of Embodiment 12 described above, wherein the laser source is a supercontinuum laser source.

Embodiment 14: The instrument of Embodiment 1 described above, further comprising an optically clear or transparent window disposed within the distal end of the cannula, the window facilitating the propagation of illumination light and laser light through the distal end of the cannula.

Embodiment 15: The instrument of Embodiment 1 described above, wherein the first optical fiber and the second optical fiber are coupled to an interior sidewall of the lumen opposite the at least one port.

The above-disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An instrument for removing subretinal fluid from an eye, comprising:
   a handle;
   a cannula coupled to the handle, a distal portion of the cannula having a curvature corresponding to a curvature of a retina of the eye, the cannula further comprising:
      a lumen extending through the cannula; and
      at least one port adjacent to a distal end of the cannula for aspirating subretinal fluid from the eye into the lumen;
   a first optical fiber extending through the cannula for propagating an illumination light through the distal end of the cannula; and
   a second optical fiber extending through the cannula for propagating a laser light through the distal end of the cannula;
   wherein the first optical fiber is joined to a third optical fiber disposed within the handle, the third optical fiber having a tapered diameter from a proximal end thereof to a distal end thereof.

2. The instrument of claim 1, wherein the cannula is formed from a material comprising a superelastic alloy.

3. The instrument of claim 2, wherein the superelastic alloy is nitinol.

4. The instrument of claim 1, wherein a proximal end of the handle comprises a Luer Lok-type connector for connecting the handle to an extrusion tubing for aspirating the subretinal fluid.

5. The instrument of claim 4, wherein the lumen is in fluid communication with a vacuum source via the extrusion tubing.

6. The instrument of claim 1, wherein the first optical fiber and the second optical fiber are nanofibers have a diameter of about 30 microns or less.

7. The instrument of claim 1, wherein the third optical fiber is joined to a fourth optical fiber at least partially disposed within the handle.

8. The instrument of claim 6, wherein the first optical fiber comprises a microlens at a distal end thereof to produce a divergent beam of illumination light.

9. The instrument of claim 1, wherein the first optical fiber is optically coupled to a light-emitting diode (LED) illumination source.

10. The instrument of claim 1, wherein the first optical fiber is optically coupled to a superluminescent diode (LED) illumination source.

11. The instrument of claim 1, wherein the second optical fiber is optically coupled to a narrowband or broadband laser source.

12. The instrument of claim 11, wherein the laser source is a supercontinuum laser source.

13. The instrument of claim 1, further comprising:
   an optically clear or transparent window disposed within the distal end of the cannula, the window facilitating the propagation of illumination light and laser light through the distal end of the cannula.

14. The instrument of claim 1, wherein the first optical fiber and the second optical fiber are coupled to an interior sidewall of the lumen opposite the at least one port.

* * * * *